(12) United States Patent
Palti

(10) Patent No.: US 10,820,890 B2
(45) Date of Patent: Nov. 3, 2020

(54) DIAGNOSING LUNG DISEASE USING TRANSTHORACIC PULMONARY DOPPLER ULTRASOUND DURING LUNG VIBRATION

(71) Applicant: Yoram Palti, Haifa (IL)

(72) Inventor: Yoram Palti, Haifa (IL)

(73) Assignee: Echosense Jersey Limited, St. Helier (JE)

(*) Notice: Subject to any disclaimer, the term of this patent is extended or adjusted under 35 U.S.C. 154(b) by 124 days.

(21) Appl. No.: 13/750,246

(22) Filed: Jan. 25, 2013

(65) Prior Publication Data

US 2014/0039313 A1 Feb. 6, 2014

Related U.S. Application Data

(60) Provisional application No. 61/591,026, filed on Jan. 26, 2012.

(51) Int. Cl.
  *A61B 8/08* (2006.01)
  *A61B 7/00* (2006.01)
  *A61B 5/0402* (2006.01)

(52) U.S. Cl.
  CPC .......... *A61B 8/488* (2013.01); *A61B 8/0825* (2013.01); *A61B 8/5207* (2013.01); *A61B 8/5223* (2013.01); *A61B 5/0402* (2013.01); *A61B 7/003* (2013.01)

(58) Field of Classification Search
  CPC ......... A61B 8/00; A61B 8/488; A61B 8/0825; A61B 8/5207; A61B 8/5223; A61B 7/003; A61B 5/0402

USPC ........................................................ 600/438
See application file for complete search history.

(56) References Cited

U.S. PATENT DOCUMENTS

| | | | |
|---|---|---|---|
| 4,646,754 A | 3/1987 | Seale | |
| 5,879,303 A * | 3/1999 | Averkiou et al. | 600/447 |
| 5,919,139 A * | 7/1999 | Lin | A61B 8/08 600/443 |
| 6,368,286 B1 | 4/2002 | Whitman | |
| 6,520,911 B1 * | 2/2003 | Wen | A61B 5/0093 600/437 |
| 2003/0032883 A1 * | 2/2003 | Aksnes | A61B 8/06 600/453 |

(Continued)

OTHER PUBLICATIONS

Stoylen Basic Ultrasound, Echocardiography and Doppler for Clinicians 2009 webpage https://web.archive.org/web/20090415000000*/http://folk.ntnu.no/stoylen/strainrate/Ultrasound/ p. 24.*

(Continued)

*Primary Examiner* — Jeffrey G Hoekstra
*Assistant Examiner* — Patrick M Mehl
(74) *Attorney, Agent, or Firm* — Potomac Law Group, PLLC

(57) ABSTRACT

Operation of a patient's lungs may be analyzed by transmitting ultrasound energy into the patient's lung, and obtain power and velocity Doppler data while a vibration is being induced in the lung. At least one portion of the power and velocity data that corresponds to a fundamental harmonic is then identified. In some embodiments, portions of the power and velocity data that corresponds to higher order harmonics are also identified. The power observed in the fundamental harmonic and optionally the higher order harmonics can then be used to determine the condition of the lungs.

20 Claims, 13 Drawing Sheets

(56) References Cited

U.S. PATENT DOCUMENTS

| | | | |
|---|---|---|---|
| 2006/0094964 A1 | 5/2006 | Ragauskas | |
| 2006/0100666 A1* | 5/2006 | Wilkinson | A61B 5/08 607/1 |
| 2007/0149891 A1* | 6/2007 | George | A61B 5/0813 600/533 |
| 2008/0139934 A1* | 6/2008 | McMorrow et al. | 600/438 |
| 2010/0010354 A1* | 1/2010 | Skerl | A61B 5/1107 600/459 |
| 2010/0063393 A1* | 3/2010 | Moradi | A61B 8/0833 600/442 |
| 2010/0280385 A1* | 11/2010 | Palti | A61B 8/06 600/454 |
| 2011/0125023 A1 | 5/2011 | Palti | |
| 2012/0101381 A1* | 4/2012 | Palti | A61B 6/06 600/438 |

OTHER PUBLICATIONS

Garrett et al. Helium gas purity monitor for recovery systems 1981 Physica 107B:601-602.*
Zhang et al. Viscoelasticity of lung tissue with surface wave method 2008 IEEE International Ultrasonics Symp. Proceed. 21-23.*
Sundberg Chest wal vibrations in singers 1983 J.Speech and Hearing Res. 26:329-340.*
Pohlmann et al. Effects of changes in lung volume on acoustic transmission through the human respiratory system 2001 Physiol. Meas. 22:233-243.*
Cavalcanti et al. Detection of changes in respiratory mechanics due to increasing degrees of airway obstruction in asthma by the forced oscillation technique 2006 100:2207-2219.*
Cavalcanti et al. Detection in respiratory mechanics due to increasing degrees of airway obstruction in asthma by the forced oscillation technique. 2006 Resp.Med. 100:2207-2219.*
Garrett et al. Helium gas purity monitor for recovery systems. 1981 Physica 107:601-602.*
Henni et al. Shear Wave Induced Resonance a new excitation mode for dynamic elastography imaging. 2008 IEEE Internat.Ultrason. Symp.Proc. 221-224.*
Parker et al. Tissue response to mechanical vibrations for "sonoelasticity imaging". 1990 Ultrasound in Med.Biol. 16:241-246.*
Pohlmann et al. Effect of changes in lung volume on acoustic transmission throgh the human respiratory system. 2001 Physiol. Meas. 22:233-243.*
Sundberg Chest vibrations in singers. 1983 J. Speech Hearing Res. 26:329-340.*
Stoylen Basic ultrasound, echocardiography and Doppler for clinicians. 2010 updated online version https://web.archive.org/web/20110824014437/http://folk.ntnu.no/stoylen/strainrate/Ultrasound/.*
Zhang et al. Viscoelasticity of lung tissue with surface wave method. 2008 IEEE Internat.Ultrasonics Symp. Proc. 21-23.*
Garrett et al. Helium Gas Purity Monitor. 1981 Physica 107B:601-602.*
Hardin et al. The clinical features of the overlap between COPD and asthma. 2011 Respiratory Res. 12:127-134.*
Omori et al. Acoustic characteristics of rough voice Subharmonics. 1997 J. of Voice 11:40-47.*
Pohlmann et al. Effect of changes in lung volume on acoustic transmission through the human respiratory system. 2001 Physiol. Meas. 22:233-243.*
Sinkus et al. Nonlinear viscoelastic properties of tissue assessed by ultrasound. 2006 IEEE Trans. Ultrason. Ferroelec. Freq. Control 53:2009-2018.*
Stoylen "Basic ultrasound, echocardiography and Doppler for clinicians" 2010 33 pages https://web.archive.org/web/20110824014437/http://folk.ntnu.no/stoylen/strainrate/Ultrasound/.*
Zhang et al. Viscoelasticity of lung tissue with surface wave method. IEEE 2008 Ultrasonics Symp. 2008 : 21-23.*
Bahoura. Pattern recognition methods applied to respiratory sounds classification into normal and wheeze classes. 2009 Comp. Biol. Med. 39:824-843.*
Cavalcanti et al. Detection in respiratory mechanics due to increasing degrees of airway obstruction in asthma by the forced oscillation technique. 2006 Respir.Med. 100:2207-2219.*
Chiappa et al. Heliox improves oxygen delivery and utilization during dynamic exercice in patients with chronic obstructive pulmonary disease.2009 Am.J.Respir.Crit.Care Med. 179:1004-1010.*
Cohen et al. Acoustic transmission of the respiratory system using speech stimulation. 1991 IEEE Trans. Biom. Engi. 38:126-132.*
Lou et al. 2011 J.Appl.Phys. 110, Aug. 31, 2001 , 7 pages.*
Raj 2005 MS Biomedical Engineering at The University of Texas in Arlington, 138 pages.*
Kuhl 2004 Nature Reviews Neuroscience 5:831-843.*
Search Report and Written Opinion from corresponding application PCT/IB2013/000090.

\* cited by examiner

DIAGNOSING LUNG DISEASE USING TRANSTHORACIC PULMONARY DOPPLER ULTRASOUND DURING LUNG VIBRATION

CROSS REFERENCE TO RELATED APPLICATIONS

This application claims the benefit of U.S. Provisional Application 61/591,026, filed Jan. 26, 2012, which is incorporated herein by reference.

BACKGROUND

Pulmonary diseases can generally be divided into obstructive and restrictive diseases. Obstructive lung diseases are diseases of the lung where the airways (i.e. bronchi, bronchioles, alveoli) become reduced in diameter or have free flow of gas impeded, making it more difficult to move air in and out of the lung. A common type of obstructive disease is the Chronic Obstructive Pulmonary Disease (COPD). Restrictive lung diseases (also known as interstitial lung diseases) are generally characterized by a loss of lung compliance, causing incomplete lung expansion and increased lung stiffness, e.g., in infant respiratory distress syndrome (IRDS). Congestive Heart Failure (CHF), which results in excess fluid in the lung, initially interstitial, may be viewed as a unique form of interstitial lung disease. Bronchitis is characterized by inflammation of the bronchial tubes (or bronchi), the air passages that extend from the trachea into the small airways and alveoli. Chronic bronchitis is associated with hypertrophy of the mucus-producing glands found in the mucosa of large cartilaginous airways. As the disease advances, progressive airflow limitation occurs, usually in association with pathologic changes of emphysema.

Trans Cranial Doppler (TCD) is a procedure in which an ultrasound beam is directly aimed at the known location of the target, without relying on imaging. As the structure and positioning of the human skull and its constituents are relatively fixed and known, specific vessels such as the arteries of the circle of Willis, at the base of the brain, are being studied in this procedure by echo Doppler alone (i.e. without imaging). The fact that the flow velocity measurements can be made without imaging enables one to do the measurements through the bones of the skull that attenuate and scatter the ultrasound beam to such an extent that practical images cannot be obtained.

While trans-cranial Doppler measurements are now in routine use to study structures in the brain, applying this technology trans-thoracically to monitor the lungs vessels was once considered impossible. This is due to the fact that the lungs contain numerous air pockets that attenuate and scatter ultrasound far more than bone. In view of this, except for the initial, large, segments of the pulmonary vessels that are not masked by lung tissue, arterial and venous flow velocity in the pulmonary vasculature and the lung tissue itself have historically not been studied by Doppler ultrasound.

The usefulness of Doppler ultrasound for monitoring the lungs was recently recognized, and is disclosed in my previously filed applications US 2011/0125023 (published May 26, 2011) and US 2012/0101381 (published Apr. 26, 2012), each of which is incorporated herein by reference. This application expands on that foundation and makes a wide range of new diagnostic tools available, all based on the use of Doppler ultrasound in the lungs.

SUMMARY

The embodiments described herein monitor the functionality of the lungs using Doppler ultrasound. It is referred to herein as "Transthoracic Pulmonary Doppler" or "TPD". In particular, the embodiments described herein monitor the functionality of the lungs using TPD while the lung is being excited by a vibration signal. Due to this vibration, the various embodiments are also referred to herein as Vibration Doppler Monitor or "VDM".

This preferred embodiments described below can be used to diagnose lung pathology and disease by monitoring signals produced during an oscillatory/resonance behavior of the lung and its various components. It should be stressed that the signals involved are not breath sounds that are a common pulmonary diagnostic means. Instead, the signal detection mechanism relies on ultrasound Doppler signals acquired from the chest surface. Conventional Doppler diagnostic systems record/monitor the movement velocity of ultrasound reflectors, primarily as related to blood flow and less often to heart muscle contraction, cardiac valve movement, etc. The Lung VDM approach described herein specifically monitors, in addition to the above, signals generated by vibrations and cyclic movement of reflecting elements, interfaces (for example the blood vessel—alveolar air, highly reflective, interface), or surfaces within the patient. These vibrations are generated as part of the VDM diagnostic procedure.

One aspect of the invention relates to a method of evaluating the functionality of a patient's lung. This method includes the step of obtaining, using an ultrasound probe that is aimed at the patient's lung, Doppler ultrasound power and velocity data, wherein the obtaining step is implemented while a vibration is being induced in the lung. It also includes the step of identifying a first portion of the power and velocity data that corresponds to a fundamental harmonic, wherein the fundamental harmonic is related to the induced vibration; and identifying at least one second portion of the power and velocity data that corresponds to at least one higher order harmonic, wherein the at least one higher order harmonic is related to the induced vibration.

Optionally, the vibration may be induced in the lung by the patient's voicing of a sound. Alternatively, the vibration may be induced in the lung by activating a transducer that is in acoustic contact with the patient's body. Preferably, in the obtaining step, the Doppler ultrasound power and velocity data is obtained for a period of time that corresponds to at least one cardiac cycle. Preferably, in the obtaining step, the vibration is induced in the lung by a signal that includes frequency components between 50 and 1000 Hz.

Additional steps may optionally be implemented, such as outputting an indication when (a) the fundamental harmonic has a frequency that exceeds a first threshold and (b) total power in the at least one higher order harmonic is lower than a second threshold. An indication may also be output when (a) the fundamental harmonic has a power that is lower than a first threshold and (b) the total power in the at least one higher order harmonic is higher than a second threshold.

Optionally, a representation of the first portion of the power and velocity data that corresponds to the fundamental harmonic may be displayed, and a representation of the at least one second portion of the power and velocity data that corresponds to the at least one higher order harmonic may also be displayed.

Optionally, a result of the displaying steps may be correlated with a condition of the patient's lung. One example is correlating a condition in which (a) the fundamental harmonic has a frequency that is much higher than expected for a normal patient and (b) total power in the at least one higher order harmonic is much lower than expected for a normal patient with a lung disease. Another example is correlating a condition in which (a) the fundamental harmonic has a power that is lower than expected for a normal patient and (b) total power in the at least one higher order harmonic is higher than expected for a normal patient with a lung disease.

Another aspect of the invention relates to a method of evaluating the functionality of a patient's lung. This method includes the step of obtaining, using an ultrasound probe that is aimed at the patient's lung, Doppler ultrasound power and velocity data, wherein the obtaining step is implemented while a vibration is being induced in the lung. It also includes the step of identifying a first portion of the power and velocity data that corresponds to a fundamental harmonic, wherein the fundamental harmonic is related to the induced vibration.

Optionally, the vibration may be induced in the lung by the patient's voicing of a sound. Alternatively, the vibration may be induced in the lung by activating a transducer that is in acoustic contact with the patient's body. Preferably, in the obtaining step, the Doppler ultrasound power and velocity data is obtained for a period of time that corresponds to at least one cardiac cycle. Preferably, in the obtaining step, the vibration is induced in the lung by a signal that includes frequency components between 50 and 1000 Hz.

Optionally, the step of measuring the fundamental harmonic after the patient inhales a known quantity of a gas (e.g., helium) may also be implemented, after which the step of calculating a lung capacity of the patient based on the frequency measured in the measuring step may be implemented.

Optionally, a first measurement of the fundamental harmonic is obtained at a first time after the patient inhales a known quantity of a gas (e.g., helium) and a second measurement of the fundamental harmonic is obtained at a second time after the patient inhales a known quantity of a gas, and a diffusion rate of the patient's lung is calculated based on the first measurement and the second measurement.

DESCRIPTION OF THE PREFERRED EMBODIMENTS

Figure 1:
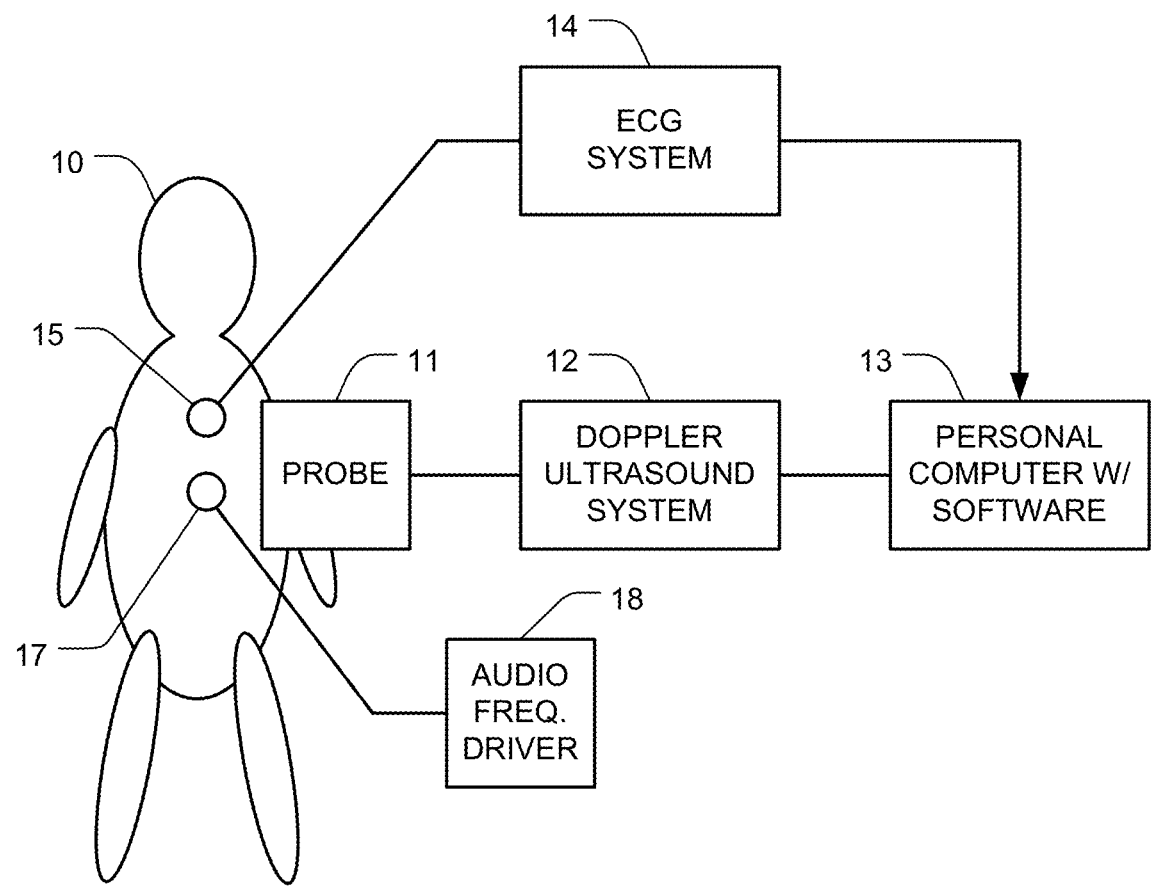
FIG. 1 is a block diagram of an embodiment of a Transthoracic Pulmonary Doppler ("TPD") System that is used to implement VDM.

FIG. 1 is a block diagram of a preferred embodiment. A Doppler ultrasound machine 12 in conjunction with the probe 11 (which includes an ultrasound transducer) is used to determine the power at every relevant velocity in a target region of the subject 10, over time, in a conventional manner. This may be accomplished by generating pulsed ultrasound beams, picking up the reflected energy, calculating the Doppler shifts, and processing the data thus obtained to provide the matrix of power and corresponding velocities of the ultrasound reflectors. One example of a suitable Doppler ultrasound machine 12 is the Sonara/tek pulsed Trans-Cranial-Doppler device (available from Viasys, Madison, Wis., US), which is a pulsed Doppler system. The Doppler ultrasound machine 12 sends the data that it captures to a personal computer 13 that is loaded with software to generate a conventional Doppler ultrasound display (e.g., on a monitor associated with the computer 13) in which the x axis represents time, the y axis represents velocity, and power is represented by color. Suitable software for controlling the ultrasound parameters is also available from Viasys. Note that in alternative embodiments, the functions of the Doppler ultrasound machine 12 and personal computer 13 may be combined into a single device.

Optionally, an ECG system 14 is also provided. The ECG system 14 interfaces with conventional ECG leads 15 and generates an output in any conventional manner. The output is preferably synchronized in time with the Doppler ultrasound machine 12 so that both an ECG and ultrasound display can be displayed on the same time scale. The output of the ECG system 14 is provided to the personal computer 13 in any conventional manner. In alternative embodiments, it may be combined by the Doppler ultrasound machine 12 instead.

A standard TCD probe such as a 21 mm diameter, 2 MHz sensor with a focal length of 4 cm may be used as the probe 11. Suitable probes are available from Viasys for use with their Sonara/tek machines. Conventional probes for making Doppler ultrasound measurements of peripheral or cardiac blood vessels may also be used. These applications, however, typically use narrow beams, often shaped using a phased array transducer, to provide a high spatial resolution that is helpful for making geometrical characterization of the relatively small targets. While these narrow beams can produce usable results in the context of TPD, some preferred alternative embodiments use relatively wide beams, for example beams with an effective cross section of at least ¼ cm² (e.g., between ¼ and 3 cm²). This may be accomplished by using a smaller transducer, and by using single element transducers instead of phased array transducers that are popular in other anatomical applications. In alternative embodiments, transducers with a relatively small number of elements (e.g., 4-6) can be used. Coin-shaped ultrasound Doppler probes (e.g., about 2 cm in diameter) are suitable for this application. When a wider beam is used, the system can take advantage of the fact that the lungs contain relatively large complexes of unspecified geometrical shape consisting of blood vessels (both arteries and veins) and their surrounding lung tissues.

Note that since imaging the lung with ultrasound is impossible because of the scattering, one has to scan for targets without guidelines, except for the known anatomy. Note also that scattering lowers the advantage of scanning by either phase array or by mechanical means. Furthermore, since the whole lung depth induces scattering, CW (continuous wave) ultrasound is less effective than PW (pulsed wave) Doppler ultrasound for pulmonary applications. Therefore, some preferred embodiments utilize PW ultrasound with relatively wide beams. Optionally, such embodiments may employ multiple sensors positioned on the surface of the body.

Optionally, specially selected or designed ultrasound probes and/or suitable beam power control may be used, including dynamic adjustable beam shape and size so as to enable measurement from variable tissue volumes. Note that in contrast to when Doppler is used for other tissue targets, here the average and integral of signals originating from relatively large volumes contain valuable information.

In addition to the standard software for generating a display from the Doppler signals, the personal computer 13 preferably includes software for activating the TPD and selecting the desired operating mode, display mode, and storage modes. The personal computer 13 also includes or has access to appropriate data storage resources (e.g., local or remote hard drives). The personal computer 13 preferably processes the original velocity-and-power vs. time data using one or more noise reduction (NR) algorithms that are optimized to minimize the noise created by the signal scattering and attenuation by the lung tissue. Two preferred approaches for implementing noise reduction are described in US 2012/0101381.

Figure 2:
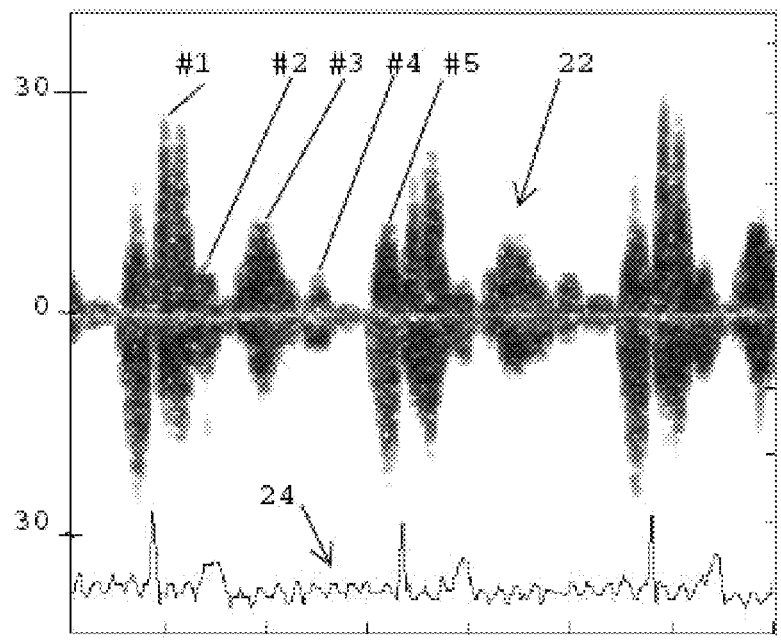
FIG. 2 depicts an example of an output generated by the system of FIG. 1 when no vibration is being induced.

After implementing noise reduction, the result is preferably smoothened via a one-dimensional median filter (e.g., of order 3) and displayed, and FIG. 2 depicts an example of the resulting output. FIG. 2 depicts the velocities 22 of the ultrasound reflectors in the right lung of a normal subject obtained using a 2 MHz Doppler ultrasound system with the probe positioned about 3 cm to the right of the sternum and 7 cm up from the level of the tip of the xiphoid bone (about the 4th intercostal space). Note that in this figure (as well as other similar figures such as FIGS. 3, 4A, 5, 6A, 6B, 10A, 10B, and 12A), the Doppler power is reflected in grayscale, the y axis represents velocity, and the x axis represents time. In real-world systems it is preferable to use color to represent power, but black and white versions are used herein for practical reasons. It is important to note that in FIG. 2, the lung is NOT being excited by a vibration signal, which explains why the horizontal lines that are present in the other figures are not seen in FIG. 2

The ultrasound beam was roughly normal to the chest surface. In FIG. 2, darker regions correspond to higher powers. A conventional ECG 24 is preferably also displayed on the bottom of FIG. 2. Similar recordings were obtained from recordings at depths (gates) of up to 14 cm and from the left lung in areas not dominated by the heart. Maximal signal strength over the right lung was recorded at a depth of 8-9 cm below the surface.

The same pulse repetition frequency (PRF) that is used in conventional TCD systems (i.e., 3-10 kHz) may be used for TPD systems. However, TPD sonograms 22 includes of a number of medium velocity signals that have the same periodicity as the cardiac cycle and usually reach values only up to about 30 cm/sec. Due to these relatively low peak velocities (as compared to Doppler flow measurements in large arteries), the TPD PRF used may be set to a value that is lower than standard pulsed Doppler systems. By lowering the PRF to between 1-3 kHz, the effective beam penetration depth can be increased. This is important as ultrasound velocity in the lung is about 30-50% lower than in fat, muscle etc. thus lowering the effective penetration depth. Preferably, the software is configured to take this lower velocity into account. The transition point where the signals originating in the lung can be detected by recognizing the shallowest point at which the lung signals (i.e., signals with very large returns) appear. Note that measurements from different lung depth result in very similar tracings, and that the traces for other apparently normal subjects had generally similar characteristics.

It is seen that, at each polarity (positive or negative), one can usually identify five significant features with relatively high energy and a roughly triangular shape. These five features are numbered #1-5 in FIG. 2. Each of these features includes a positive component (i.e., positive velocities, indicating that the flow direction is towards the probe) and a corresponding negative component (i.e., negative velocities, indicating that the flow direction is away from the probe), with a high degree of positive/negative symmetry. Thus, each of these features indicates simultaneous movements in opposite directions. The five features #1-5 are synchronous with the cardiac cycle (note the ECG 24).

A theory of operation for the signals that appear in FIG. 2 is provided in US 2012/0101381. And as explained in that application, it is notable that with conventional Doppler measurements of blood flow through vessels, where the movement is the blood flow itself, the probes are positioned so the ultrasound beam is as parallel as possible to the flow axis to obtain maximal velocity. In contrast, the motion that gives rise to the TPD measurements described herein is perpendicular to the direction of blood flow, so the optimal position is normal to the flow axis and parallel to the vessel radius. But since there are so many blood vessels in the lungs, positioning is less critical in the context of TPD (as compared to conventional Doppler measurements of blood flow through vessels). The recorded signals are referred to herein as Lung Doppler Velocity Signals, (LDVS).

The situation changes dramatically when the lung is excited by a vibration signal. There are two preferred ways to apply the vibration signal to the lung. One is by having the patient voice a sound such as "Eee" or "Ahh." The second is by activating a transducer 17, shown in FIG. 1 (e.g., a loudspeaker) that has been placed in acoustic contact with the patient's chest and driving the transducer 17 with a signal from an audio frequency driver 18 that induces a vibration.

Figure 3:
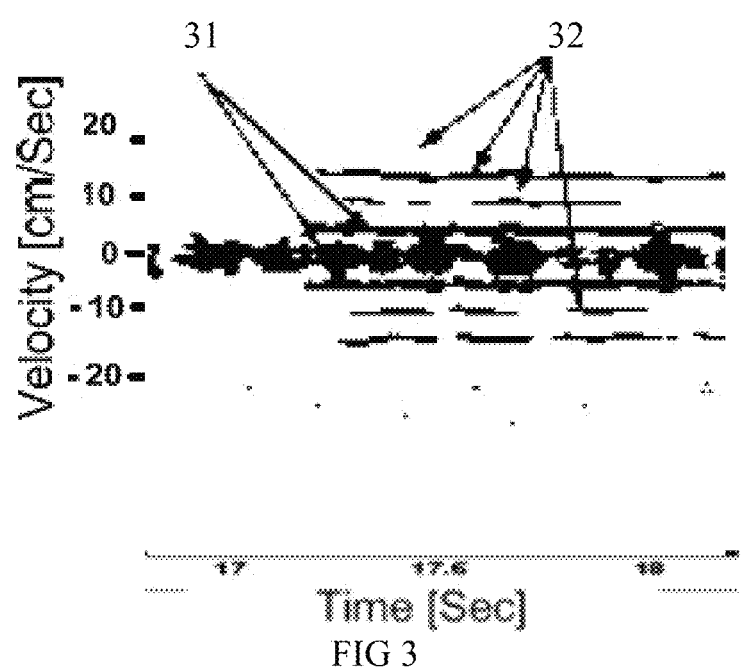
FIG. 3 depicts an example of an output generated by the system of FIG. 1 when a vibration is being induced in the lung.

FIG. 3 depicts how the TPD output changes when the former approach is used. In particular, FIG. 3 shows the output that is produced when the patient sounds an "Ahh" sound with his voice. In contrast to FIG. 2 which does not contain any horizontal lines, the VDM tracing in FIG. 3 includes of a series of equally spaced horizontal lines 31, 32 of relatively high reflected power. The lines appear symmetrically at the two sides of the zero line and their power intensity diminishes with distance from the zero line. Notably, there is no correlation between the appearance of these signals and the heart beat. We will refer to these horizontal lines as "Harmonic Resonance Lines" or HRs. The HRs normally do not appear spontaneously over the lungs, rather are initiated by a mechanical "stimulus" which is part of the procedure. The lines appear to resemble a fundamental harmonic 31 and higher-order harmonics 32.

Figure 4A:
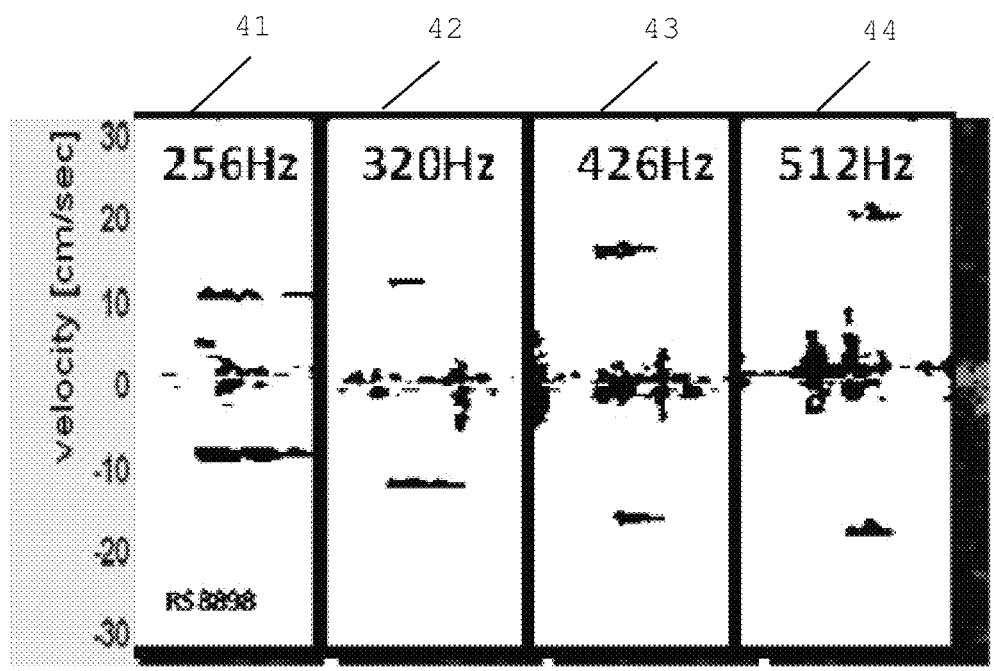
FIG. 4A depicts four data points that map velocity onto frequency and FIG. 4B is a summary plot of those data points.

To understand the significance of the HRs, an experiment was performed. Tuning forks with four different frequencies (256, 320, 426, and 512 Hz) were placed in contact with the patient's body so as to induce a vibration, and the TPD output was observed. The results of that experiment are depicted in FIG. 4A, In each case 41-44, the TPD output included just a single pair of HRs symmetrical with respect to the zero line—one HR at a particular positive velocity, and a counterpart HR on the corresponding negative velocity. The vertical lines (perpendicular to the HRs) presumably reflect lung Doppler signals and possibly artifacts.

Figure 4B:
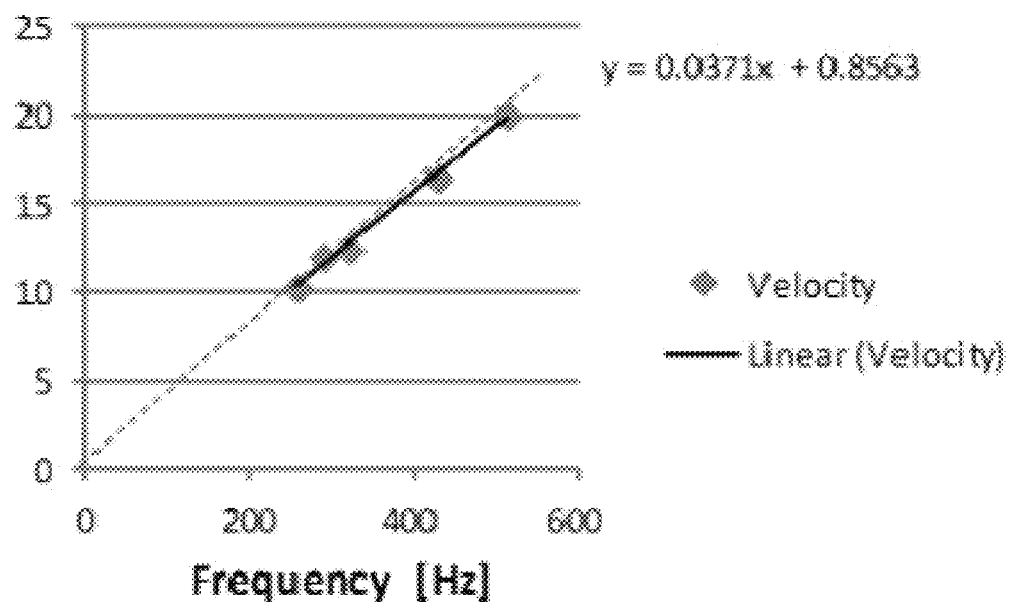

Here, each HR corresponds to a specific Doppler velocity (which can be read on the Y-Axis), and these velocities are referred to herein as "HR Velocity", or HRV. And notably, the Doppler velocity of each HR was proportional to the fundamental frequency of the specific tuning fork. When the velocity of the HRs in the four tests were plotted against the frequency of the tuning fork, as seen in FIG. 4B, the data revealed that a linear relationship exists between the frequency of the running fork and the velocity of the HR on the TPD display. In particular, the velocity V is related to the frequency x by the equation $V=0.0371x+0.8563$. This linear relationship can serve as a calibration curve by means of which the frequency of all HRs (HRV) can be determined. As a result of this calibration curve, the various Doppler velocities and the frequencies of the vibration can be mapped onto one another and used as surrogates for one another. For example, many of the plots depicted herein contain two scales—one for Doppler velocity and one for vibration frequency. The same TPD display can be read using either scale due to the mapping between those two concepts. See e.g., FIG. 5, in which the velocity scale appears on left and the frequency scale appears on the right.

Figure 5:
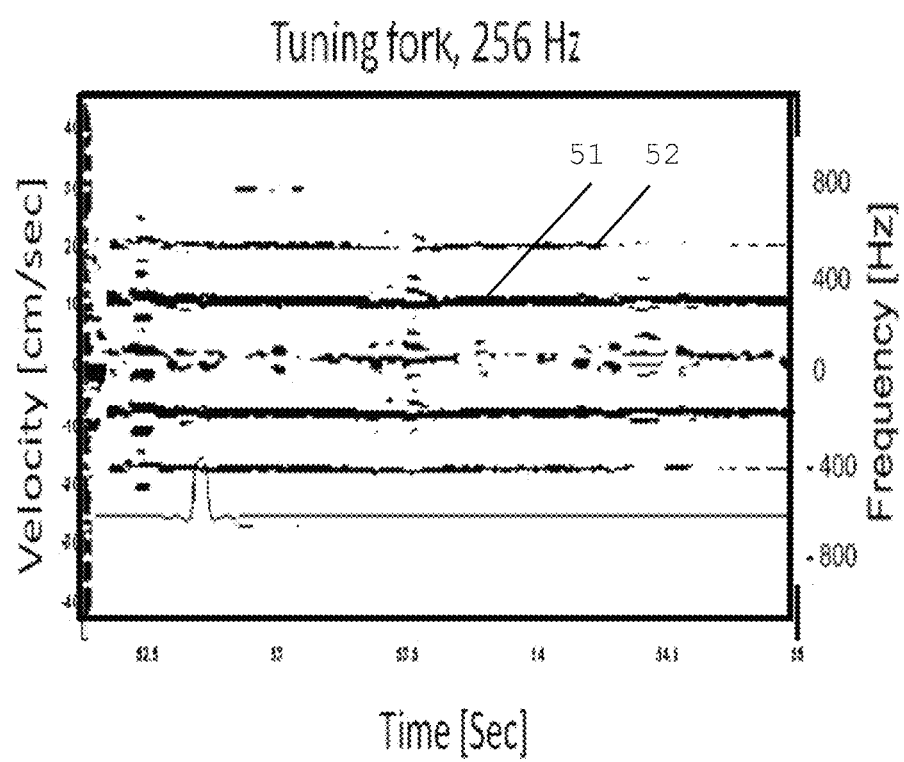
FIG. 5 depicts another example of an output generated by the system of FIG. 1 when a vibration is being induced in the lung.

The HR lines described above in connection with FIG. 4A relate to the expression of the induced single frequency vibration, in a calibration mode, that travels in the body (mainly along rigid or bony structures) and eventually reaches the VDM sensor. But a different result may be obtained when the vibration frequency has specific values that are close to a resonant frequency of the patient's body. In FIG. 5, for example, we see a recording over the lung when the vibration frequency was 256 Hz in the case when that frequency matched a resonance in the patient. In this case we see a number of HRs spaced at regular intervals along the Y-Axis. If we ignore the negative values, the lowermost HR 51 that has the strongest power (i.e., the darkest line) corresponds to the first harmonic (i.e., the fundamental harmonic) while the other HRs 52 correspond to the second, third, fourth, etc. harmonics, referred to collectively herein as "higher order harmonics".

The observed response, with multiple HRs, is expected to be elicited when the frequency of the tuning fork is equal to or close to a resonant element within the body. The harmonics have frequencies that are multiples of the fundamental frequency, i.e. corresponding to the $2^{nd}$, $3^{th}$, harmonic, etc., and the relationship between the harmonic series is the same as the relationship in air-filled tubes that are open at each of its two ends.

Multiple HRs are practically always obtained when the vibration source is the subject's own voice or selected vibrating elements that include a broad band of frequencies. In such cases the vibration frequency content has a relatively very wide spectrum (Physics Fundamentals by Vincent Coletta, 2010). Such a recording obtained over the right lung from a subject voicing "Ahh" and "Eee" sounds, respectively, is presented in FIGS. 6A and 6B.

Figure 6A:
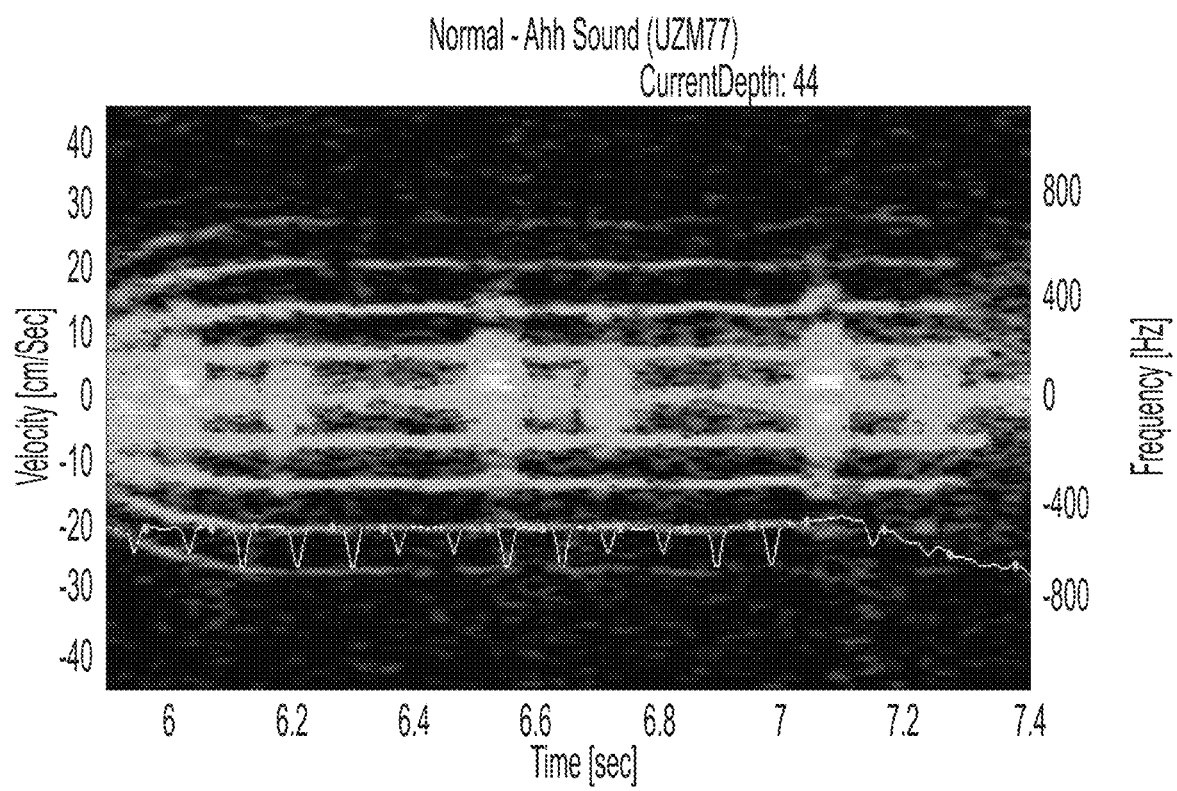
FIGS. 6A and 6B depict Doppler power and velocity vs. time data obtained when two different sounds are being voiced.
Figure 6B:
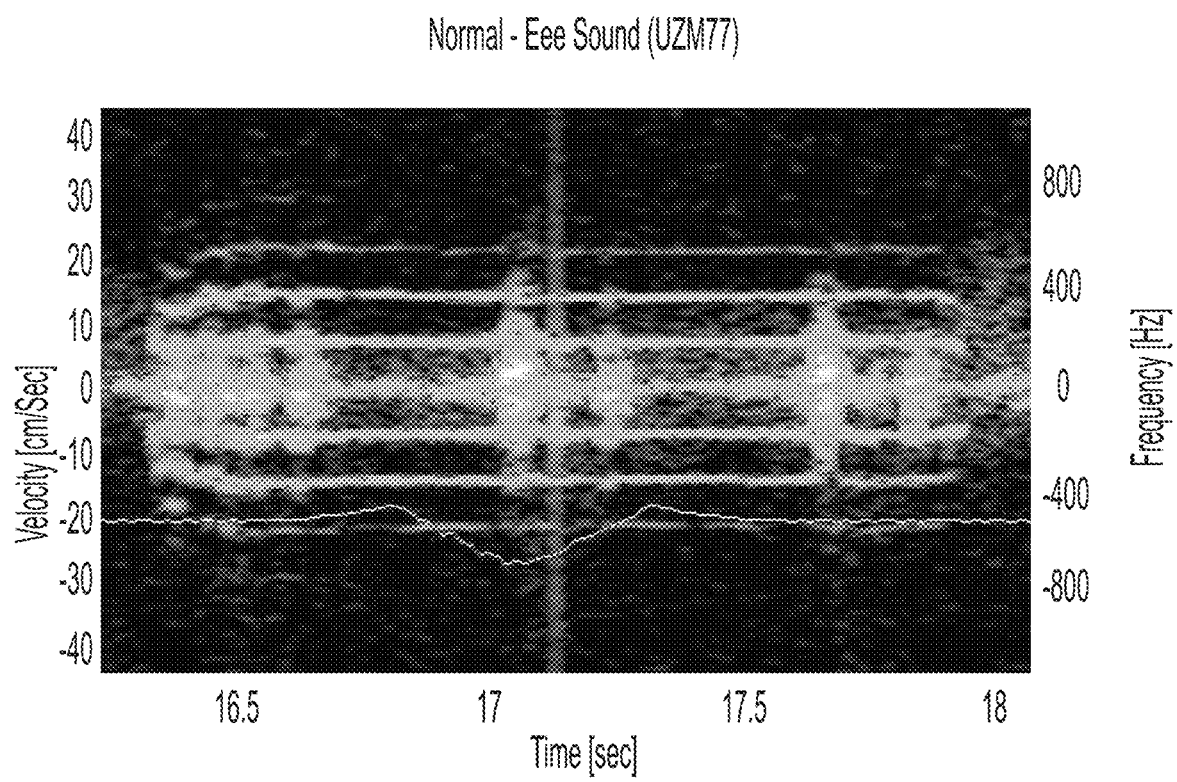
Figure 6C:
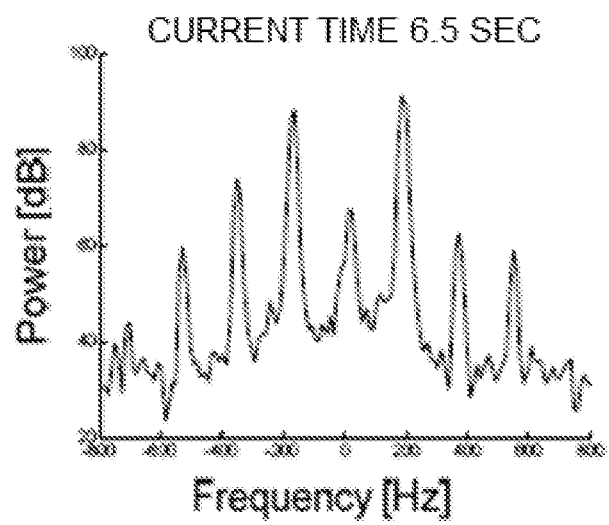
FIGS. 6C and 6D depict power spectra that correspond, respectively, to the data in FIGS. 6A and 6B.
Figure 6D:
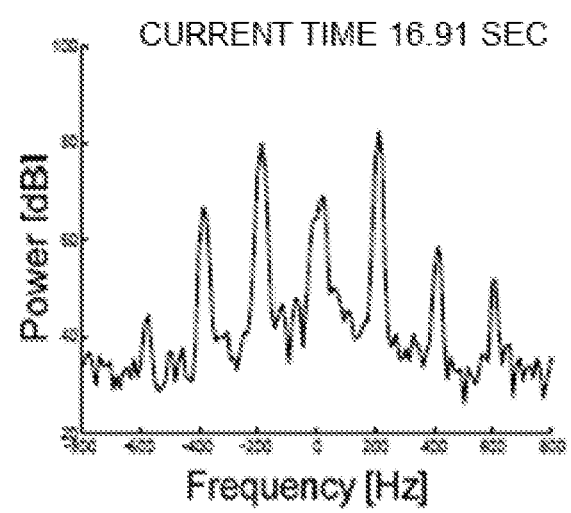

FIGS. 6A and 6B depict HR lines corresponding to a fundamental harmonics of about 200 Hz for the Ahh sound and about 250 Hz for the Eee sound. Note that when a very high singing pitch is used to voice the sound, it produce HRs (not shown) of more than double of these frequencies, depending on the state of the lung bronchi and parenchyma. In addition we see at least two additional HR 62, 67 for each sound, which correspond to second and third harmonics (400 & 600 Hz Ahh, for example). The power of the fundamental frequency 61, 66 is almost always the highest and, as expected, the power diminishes with the harmonic order. FIGS. 6C and 6D are examples of the power spectrum display of the VDM that depicts the frequency and relative power content of the HRs that are visible in FIGS. 6A and 6B, respectively.

The above results indicate that the chest cavity over which the VDM probe is placed contains elements that vibrate and under proper "stimulating" conditions resonate. Modeling the lungs as a set of air filled branching pipes (unlike those in a pipe organ) appears to fit the data. It is well known that the fundamental resonance frequency of a string or a pipe (as that of an organ) is a function of its length. The shorter the length of the resonating element, the higher the frequency of the resonance. If the signals recorded by the VDM represent the resonance of the lung bronchi, the resonance frequency must be mainly a function of the length of the bronchi.

The inventor has recognized that the resonances of the lungs will change based on the condition of the lung. Because of this, it becomes possible to evaluate the condition of the lungs by monitoring changes in the resonances (e.g., by comparing the relative strengths of the fundamental HR and the higher order harmonics).

Figure 7A:
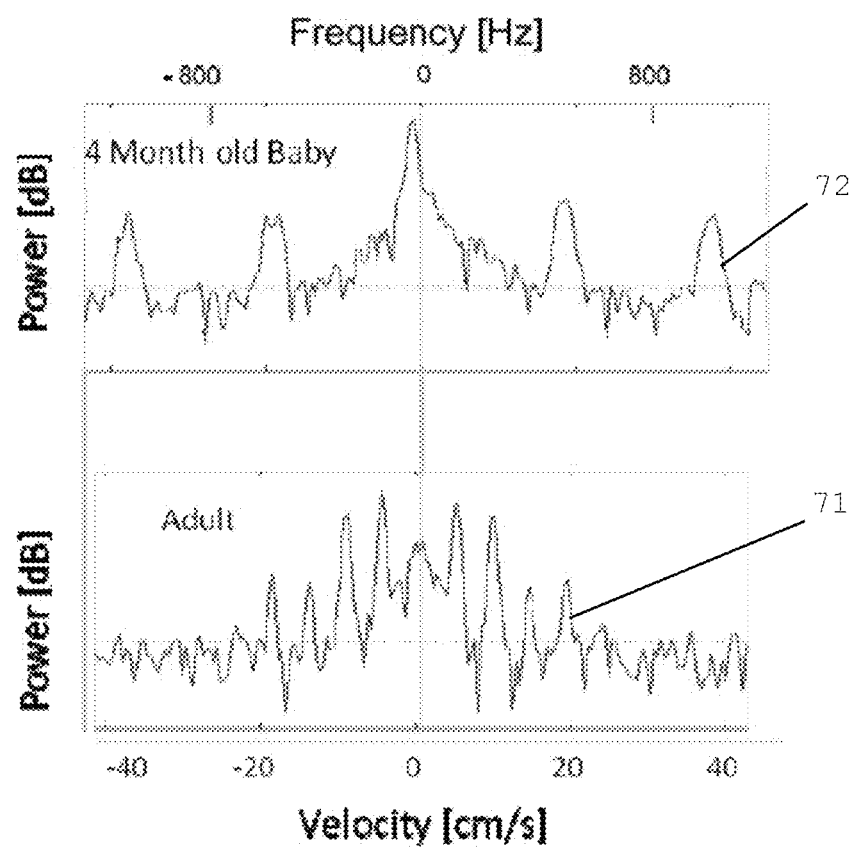
FIG. 7A depicts the power spectra for sounds made by a baby and an adult.

FIG. 7A depicts power spectra that were generated from TPD signals obtained from the lungs of an adult 71 and the lungs of a four month old baby 72, respectively. These power spectra illustrate how the state of the lungs can be evaluated from changes in the observed resonances, because in the case of the baby the fundamental frequency is about 500 Hz while that of the adult is about 130 Hz, as expected from their corresponding lengths (since the baby's bronchi are much shorter).

Note that the classical equations describing the length/frequency relationship do not apply to the bronchial tree as it consists of multiple tubes and bifurcating tubes. The relative power of the different harmonics is known to depend on the nature of the pipe walls as well as the surroundings, in our case the lung parenchyma and other chest structures, as well as the chest dimensions structures (the "resonance box"). Thus, the harmonic content and their relative size can serve to detect changes from their normal structure, i.e. diagnose pathologies and diseases.

Figure 7B:
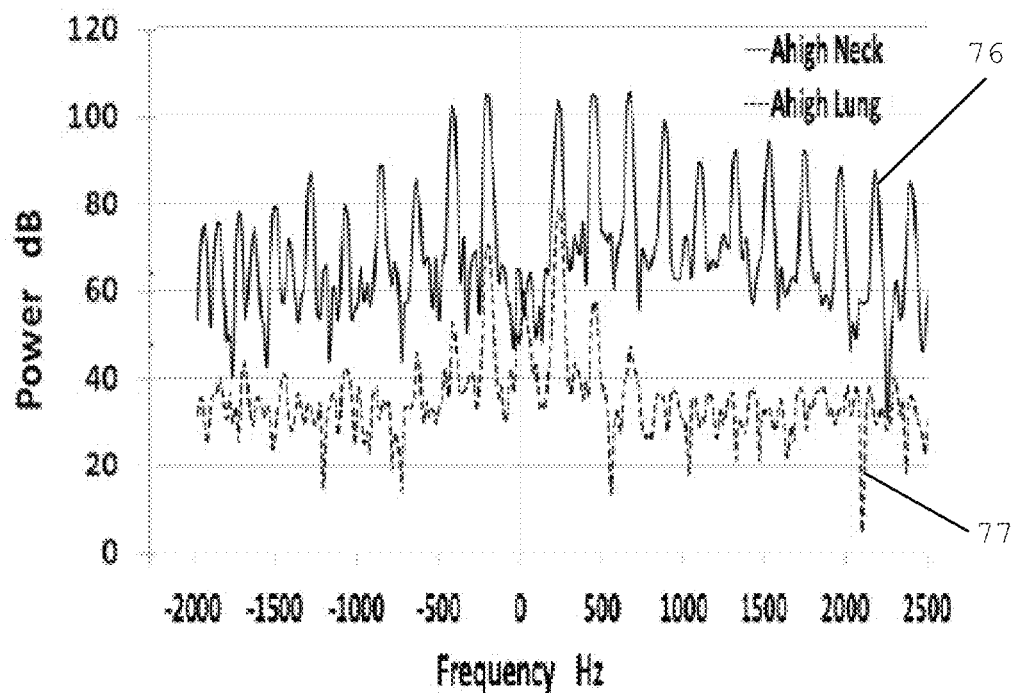
FIG. 7B depicts an input signal and lung resonances that result from that input signal.

Another example that illustrates how the state of the lungs can be evaluated from the observed resonances using the TPD signals can be found by comparing the frequency content of the TPD signals obtained from the lungs to the frequency content of the driving signal that ultimately resulted in those TPD signals. More specifically, in FIG. 7B the solid line 76 shows an example of a driving signal that was used to excite the lungs by having the patient sound a high pitch "Ahh" sound, as recorded over the vocal cords. Note the presence of many harmonics with significant power all the way out to the 11th harmonic. Then, compare this driving signal 76 with the TPD output signal 77 that is obtained from the lungs. Here, only the fundamental harmonic and the second and third harmonics are significant. And the fourth harmonic and all higher harmonics are dramatically reduced with respect to the driving signal. Since the bandwidth measured over the lungs is much narrower than the bandwidth of the driving signal, we see once again that the state of the lungs impacts the observed resonances.

Figures 8A, 8B, 8C:
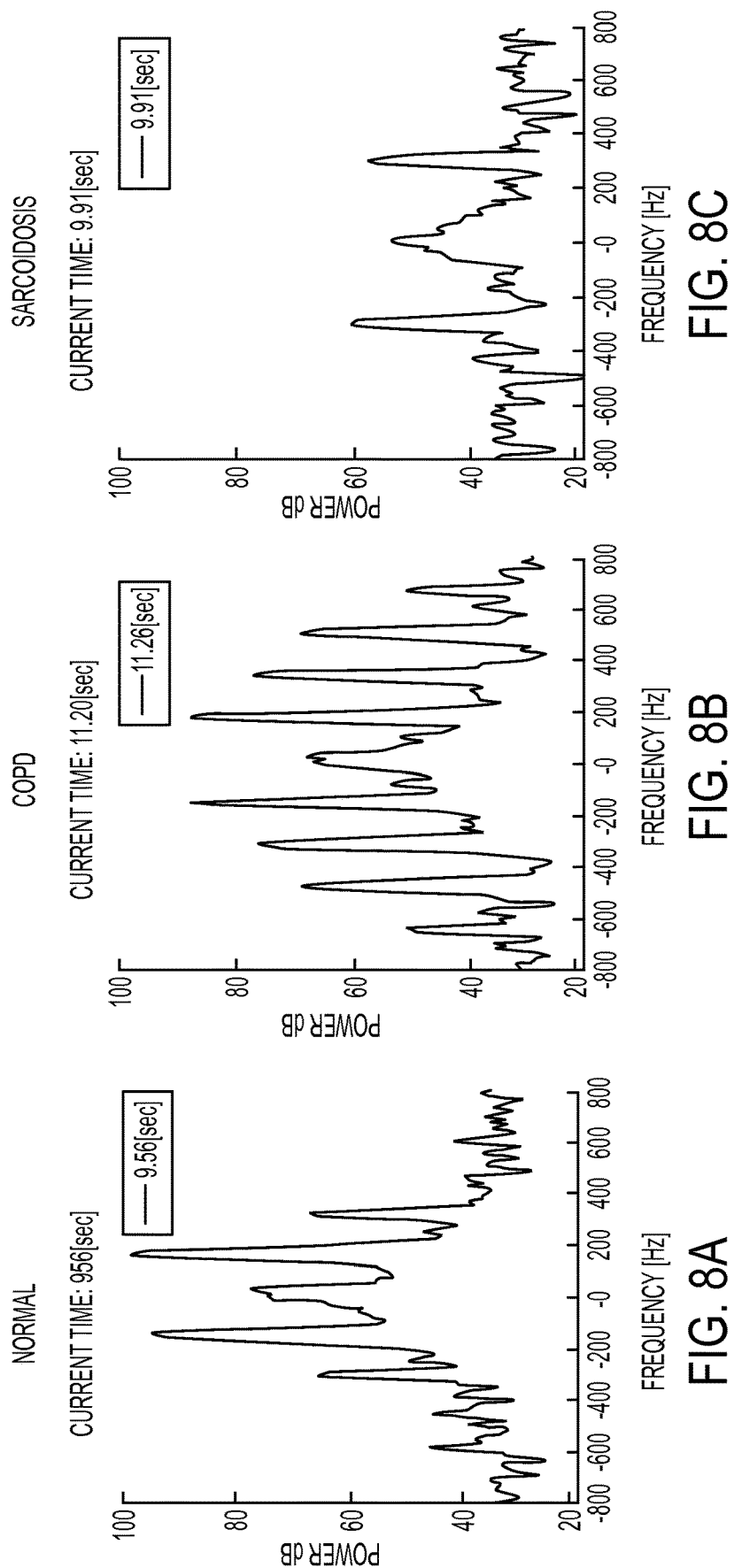
FIGS. 8A, 8B, and 8C depict examples of power spectra for three different patients.

Because the observed resonances convey information about the state of the lungs, changes in those resonances can be used to diagnose lung disease. FIGS. 8A-C compares power spectra of the vibration recordings made on a normal subject (FIG. 8A) with those made on patients with COPD (FIG. 8B) and sarcoidosis (FIG. 8C). We see that the fundamental frequencies and the amplitude of the harmonics are quite different illustrating the diagnostic power of the VDM device and methodology. For example, as compared to the normal patient, the COPD patient (FIG. 8B) has less power in the fundamental harmonic and comparatively more power in the higher order harmonics. And as compared to the normal patient, the sarcoidosis patient (FIG. 8C) has hardly any power at all in the higher order harmonics.

Figure 9:
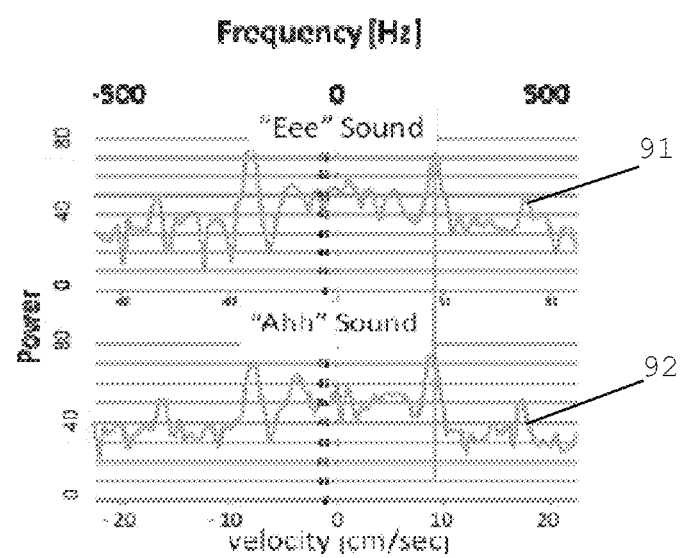
FIG. 9 depicts additional power spectra for a different patient.

FIG. 9 depict the power spectra obtained from a patient suffering from acute bronchitis in the smaller more distal bronchi (bronchiolitis), when sounding an Eee sound 91 and an Ahh sound 92. When these spectra are compared to the spectra from normal lungs situation (depicted in FIG. 8A), two differences are apparent: First, the fundamental harmonic in the bronchitis example has higher velocity (i.e. frequency) of about twice the normal value. In addition while the power spectrum from the normal lungs has significant power in the first (i.e., fundamental), second, and third harmonics, all the higher order harmonics are severely attenuated in the bronchitis lungs—so much so that that they are barely noticeable. These characteristics are likely to indicate that in this case the swelling, infiltration, and excretions in the relatively small bronchi change their acoustic properties such that the amplitude of the higher order harmonics is lower and the more dominant resonances are those of the smaller and shorter pipes that have higher resonant frequencies. These distinctions make the VDM system very useful for diagnosing the various diseases.

Variations in power of the various harmonics can provide information regarding the function of the lungs as well as their structure, and the values obtained for each harmonic will depend on features such as cavity length, mechanical properties of the tube wall, diameter of the tubes, the nature of the inflammation, and properties of the surroundings. These differences can be used to diagnose the diseases discussed herein as well as other pulmonary diseases based on a visual inspection of the original power/velocity displays generated by the TPD system, or based on a visual inspection of the power spectra that are derived from the original power/velocity data. In alternative embodiments, the features noted above or other relevant features may be recognized using appropriate pattern recognition software to make such diagnoses automatically.

One suitable approach for automating a diagnosis is to obtain TPD signals while inducing a vibration as described above. The TPD signals are then analyzed to recognize the fundamental harmonic and any higher-order harmonics. The harmonics are then correlated with prevailing special conditions (e.g., lung air pressure, body position, Vibrator freq. etc.). Classification Features may be established and the harmonic data can then be fed into the classifiers. This process is then repeated until an optimal classification is obtained. A diagnosis may then be established based on the classification.

Figure 10A:
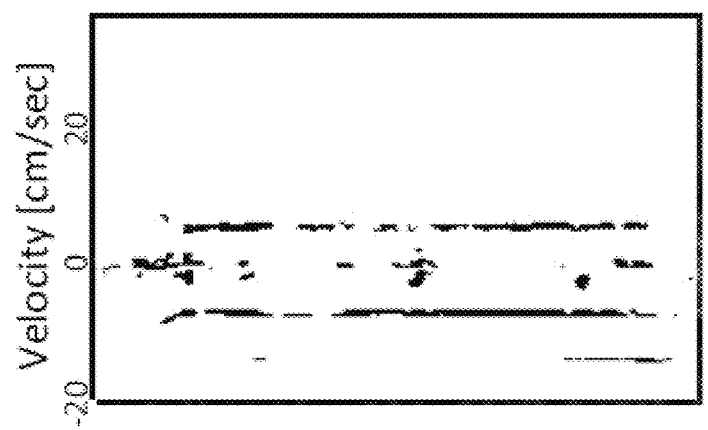
FIGS. 10A and 10B depict Doppler power and velocity vs. time data obtained before and after a medication is administered.
Figure 10B:
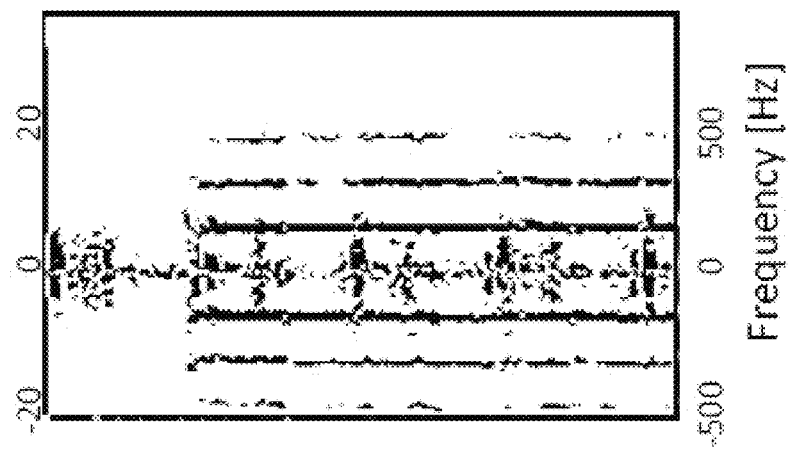
Figure 10C:
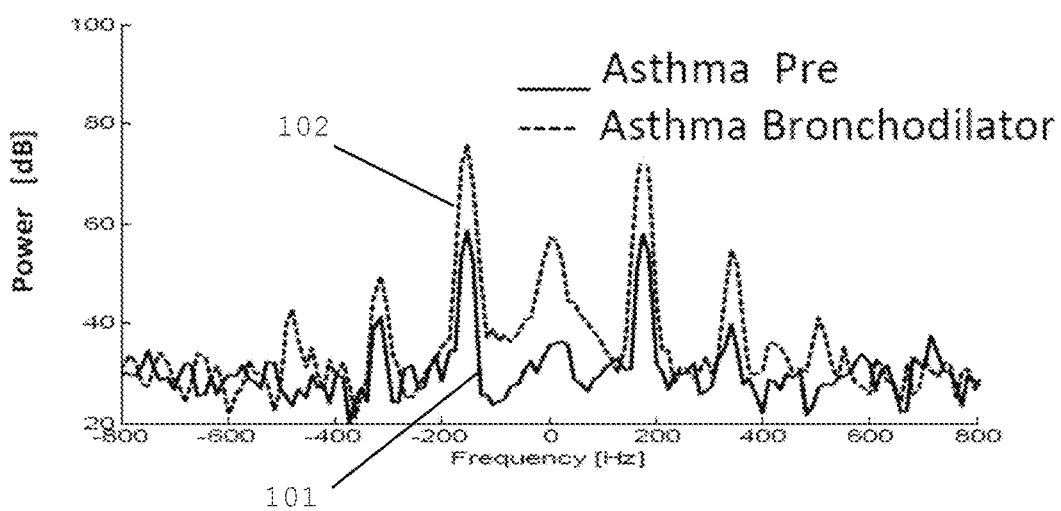
FIG. 10C depicts power spectra that correspond to FIGS. 10A and 10B.

The TPD system can also be used to monitor changes in the lungs that occur in response to the administration of medications. For example, FIGS. 10A and 10B depicts VDM Recording of Doppler velocity of vibrations generated in the chest by sounding Ahh and the corresponding Power Spectrum 101, 102 from a patient suffering from Asthma, both before (FIG. 10A) and after (FIG. 10B) the administration of bronchodilator. We see that the HR lines become significantly more pronounced after the administration of bronchodilator. The corresponding power spectra 101, 102 seen in FIG. 10C demonstrate that the HR frequencies themselves do not change. But after the administration of bronchodilator the power of fundamental harmonic increases by about 20 dB and additional higher order harmonics become visible. These results are consistent with fact that the bronchi length does not change when a bronchodilator is administered, but their diameter and their structure, as well as environment, do change.

Figure 11A:
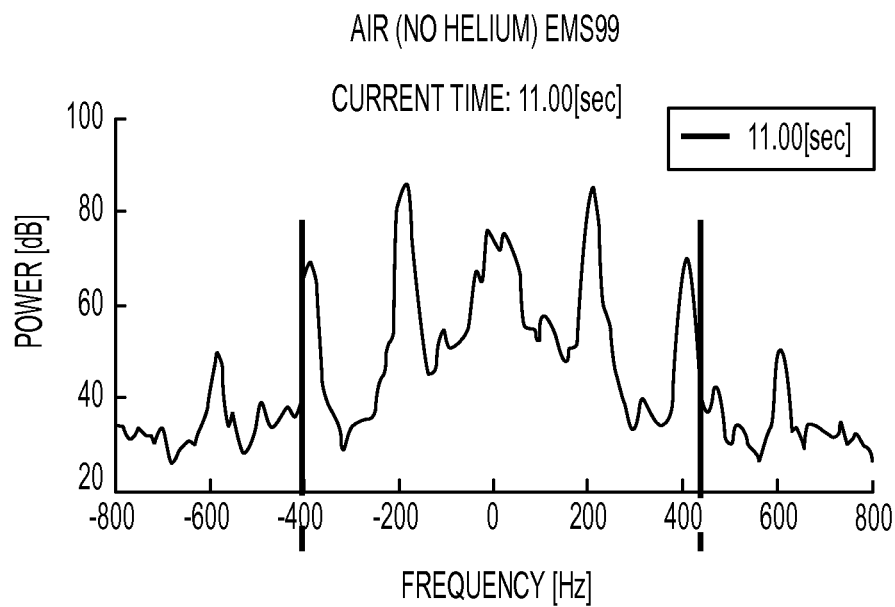
FIGS. 11A-D depict power spectra that were obtained in the presence and absence of added Helium.
Figure 11B:
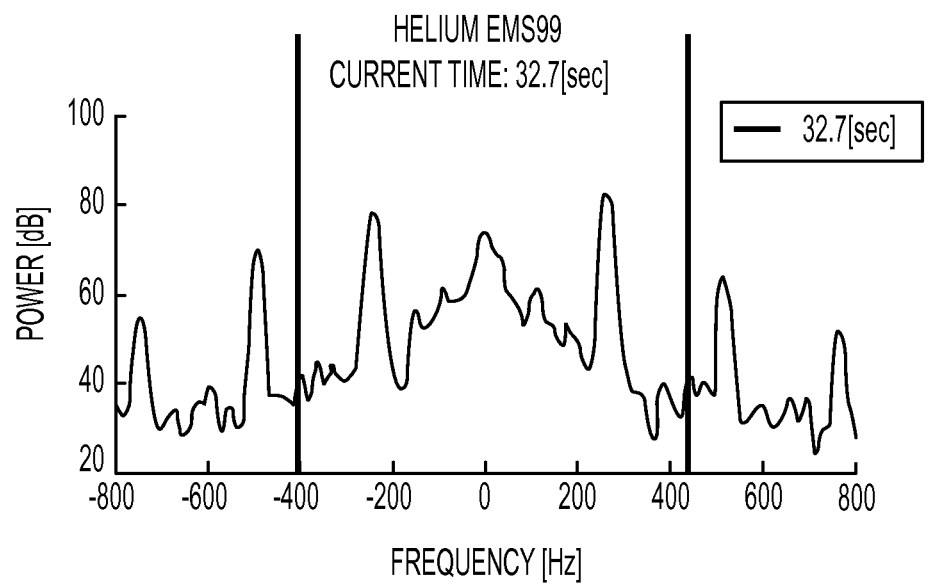

The TPD system can also be used to monitor changes in the lungs that occur when certain gases are inhaled. As a control experiment, the observed resonances of the lungs were compared in a healthy lung filled with air and in the same lung filled with a mixture of air and helium, and the results are depicted in appear in FIGS. 11A and 11B, respectively. (In the case of FIG. 11B, the subject had inhaled about 500 cc Helium, which resulted in a lung gas He concentration of about 10%.) A comparison of FIGS. 11A to 11B reveals that the resonances all shifted up by about 20% towards higher frequencies. Notably, this shift is also consistent with modeling the lungs as a set of air filled pipes, because the resonant frequency of an air filled pipe is linearly related to the sound velocity in the gas filling the pipe and the sound wave propagation velocity in He is about 3 times that in air.

The last property can also serve as a means to use the VDM as a tool that performs Pulmonary Function Tests, PFT. PFT mainly consists of three types of measurements: lung volumes, timed expiration air flow rates and diffusion rate of gases from the lung to the blood. As the resonant frequency is a function of the percentage of He in the inspired air, when one inhales a known quantity of He (this can be achieved e.g., by inhaling from a bag of a given volume or through a gas flow meter), the percentage of He is determined by the prevailing total lung volume so that one can calculate the lung volume from the frequency shift as determined by the VDM. The VDM is performed in these cases of lung function tests as follows: the subject inhales a known volume of He when his lung volume is at one of a number of physiological states the volume of which is to be determined (e.g., max expiration, end of expiration, or inspiration during tidal volume respiration, etc.) The He volume mixes with the prevailing lung air such that from its final concentration (e.g., 10%), one can compute the lung volume with which it mixed. Such computation will use a calibration curve which gives the HR shift for a given He concentration. For example, for total lung capacity, the subject performs max inspiration, exhales a known air volume (into a bag or through a flow meter) and then inspires a known volume of He while being monitored by the VDM.

Lung volume can be computed as follows: The speed of sound in air is about 350 m/s and the speed of sound in pure helium is about 1050 m/s. For a mixture of X percent air and (1−X) percent helium, the speed of sound V in the mixture is governed by the following formula $$X=-0.904+5.33*10^4 V^{-2}+[0.554+1.98*10^5 V^{-2}+1.428*10^7 V^{-4}]^{0.5}$$

Since the resonant frequencies map onto velocity, as explained above, the percentage of Helium that is contained in the lungs can be computed based on the formula above when the resonant frequencies are observed from the TPD data.

Then, once the percentage of Helium is determined, the total volume of the lung Vol(lung) can be computed using the following formula, based on the assumption that a known volume Vol(He) of helium was inhaled. Note that $$Vol(lung)=7.25*Vol(He)*X/(1-X)$$

Figure 11C:
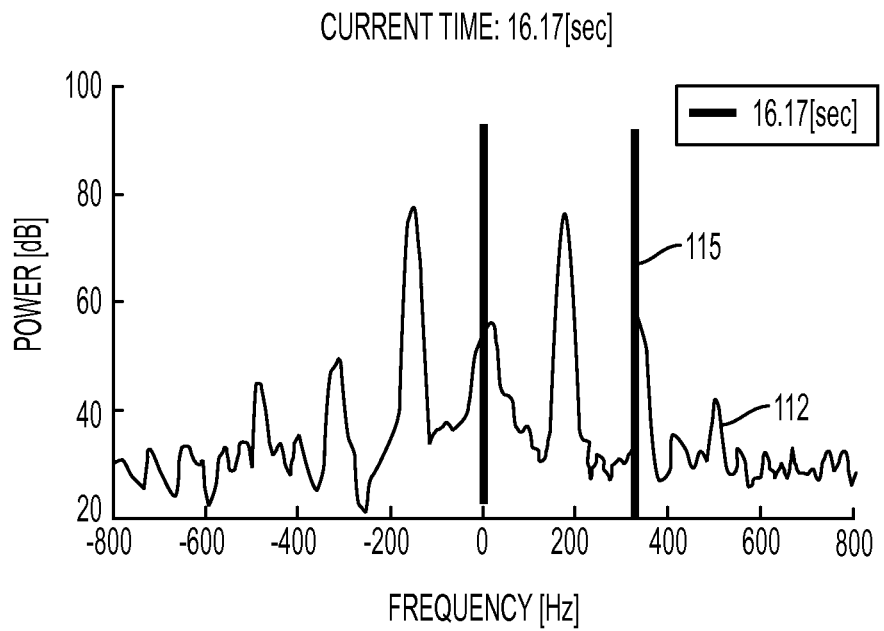
Figure 11D:
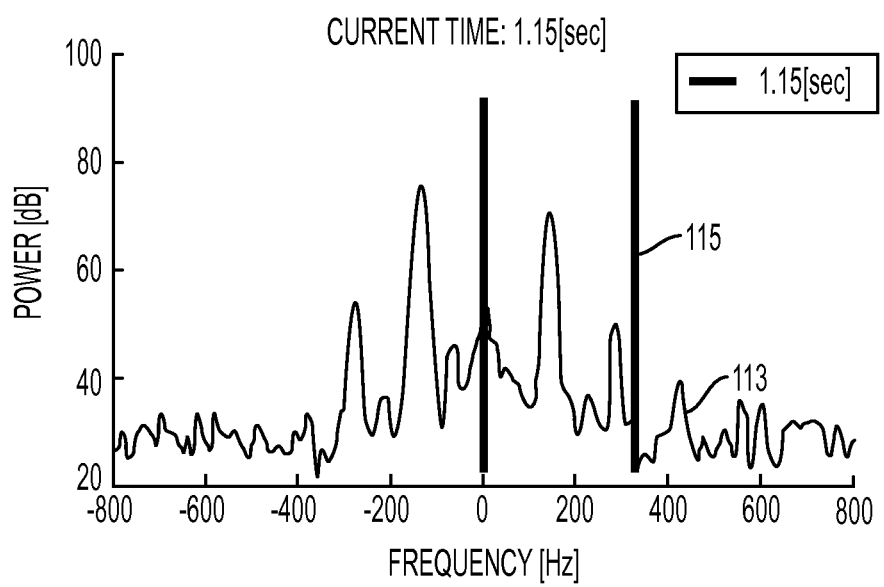

A Diffusion rate test may be performed as follows: The subject inhales a known volume of He and then holds his breath while being monitored by the VDM. The He diffuses through the "lung-blood barrier/membrane," dissolves in the plasma and subsequently is carried away by the large volume blood flow such that the blood He concentration is effectively zero at all times, i.e. the He concentration gradient which determines the diffusion rate is determined by the lung He concentration alone. Note that the above condition holds true only for relatively small He volumes or short testing times as large volumes or exposures may bring the He blood content to saturation so that incoming blood may contain He. As the lung He concentration can be determined by the frequency shift, the effective "lung-blood barrier/membrane" diffusion constant can be calculated. FIGS. 11C and 11D are power spectra 112, 113 obtained using TPD that illustrate such a test, with FIG. 11C depicting the shifted HR frequency just after the He inhalation; and FIG. 11D depicting the results 20 sec later when virtually all the He has diffused out of the subject's lungs, and the frequency has returned to the baseline level (about 40 Hz lower than that in FIG. 11C). The two pairs of vertical reference lines 115 are spaced at the same distance from each other in both figures to aid the evaluation of the frequency change. Preferably, the fraction/volume of HE is determined (from the resonant frequency) immediately (1-2 sec) after the He breathing as the diffusion rate of He is much faster than that of CO.

Figure 12A:
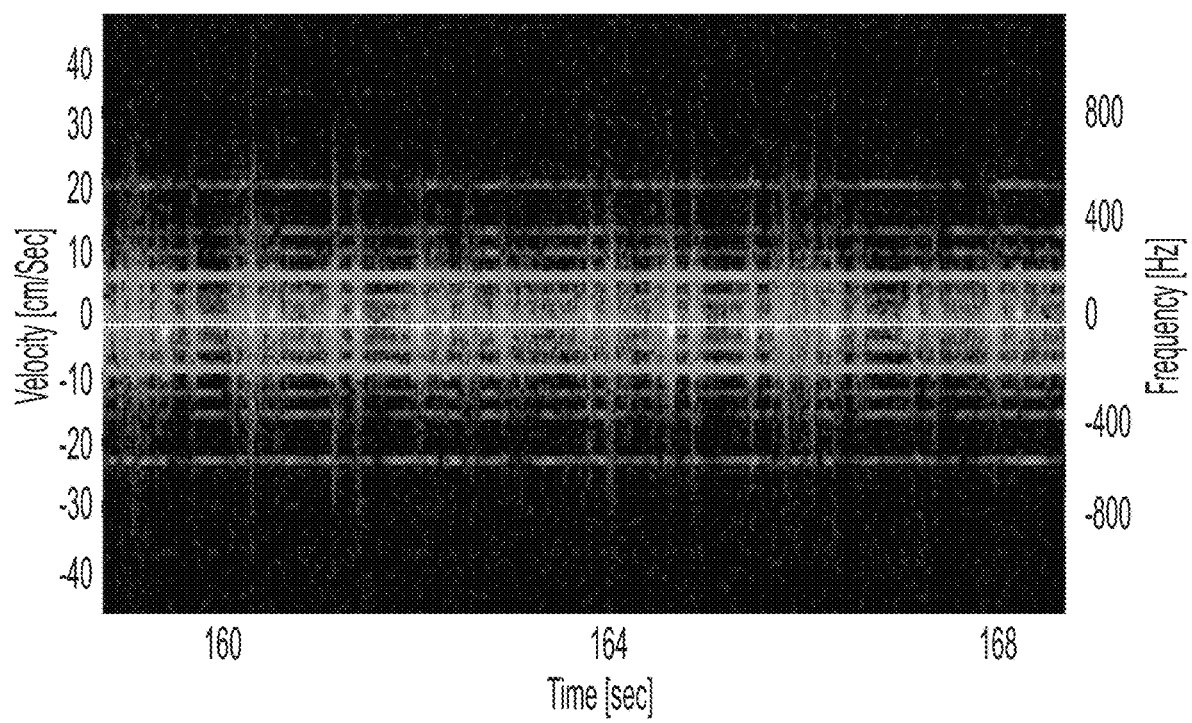
FIG. 12A depicts Doppler power and velocity vs. time data obtained when an external vibration source is used
Figure 12B:
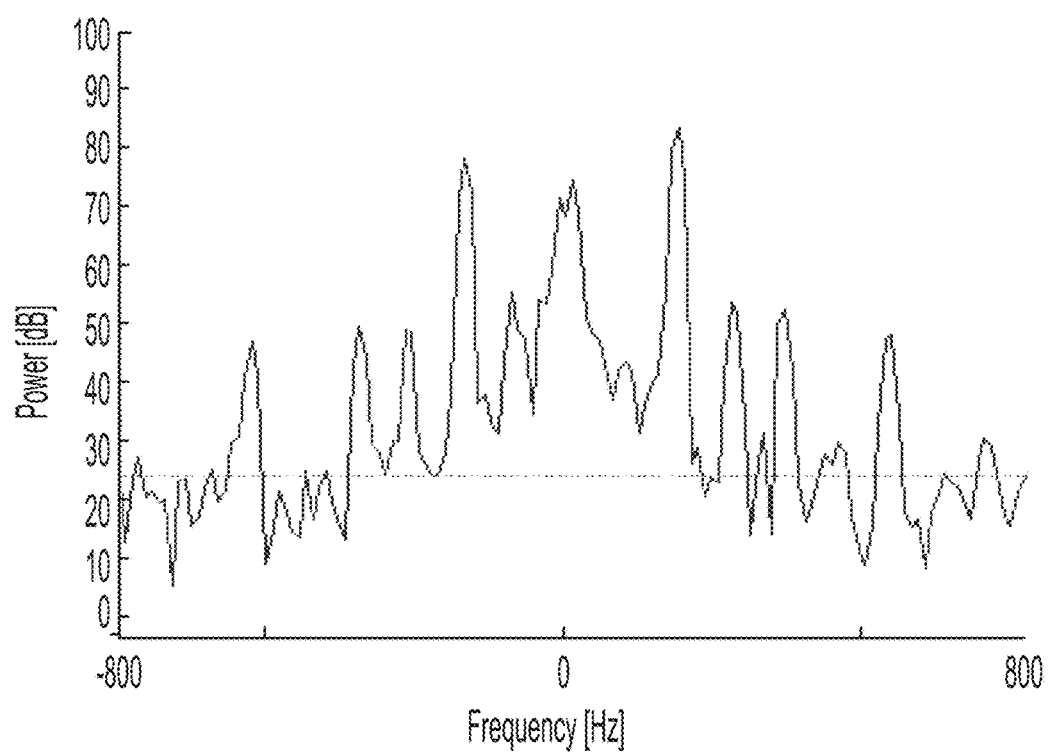
FIG. 12B depicts a corresponding power spectrum.

Note that in the embodiments described above, vibration in the lungs was induced by having the patient voice a sound like "Ahh" or "Eee." However, in alternative embodiments, a vibrating transducer element (piezoelectric, audio speaker 17, electromagnetic sound generator, etc.) can be placed in contact with the subject, and driven by the output of an appropriate wave function generator instead. Preferably, the transducer is positioned on the subject's skin at one of the designated locations (for example, over the distal part of the radial bone, elbow, clavicle, sternum, etc.), and the frequency content of the sound generated by the vibrating element, as shaped by a function generator, should preferably include the lung resonant frequencies, which are generally within the audio frequency range (e.g., about 50-1000 Hz). A broad band signal is most preferably used to induce the vibration because it permits the natural resonances of the lungs to appear. Most preferably, the signal contains power in the audio frequency range (e.g., 50-1000 Hz). FIG. 12A is an example of the Doppler power and velocity data obtained when such a vibrating transducer element is used and FIG. 12B depicts a corresponding power spectrum.

Theoretically an induced vibration is of sinusoidal shape. However, in practice the mechanical wave shape is usually somewhat distorted. In our case the distortion of the high velocity fraction of the wave is expressed by the height and width of the harmonic power signal in the power spectra while the low frequency components are expressed in the baseline power elevation around the zero frequency line (see e.g., FIG. 6). All these features reflect changes in the mechanical properties of the vibrating and reflecting components and thus can serve in disease diagnosis.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of evaluating the functionality of a patient's lung, the method comprising the steps of:
    setting up an audio frequency driving signal in the patient's lung by having the patient voice a sound or by activating a transducer;
    obtaining, using an ultrasound probe that is aimed at the patient's lung, Doppler ultrasound power and velocity data that represents movement of interfaces between blood vessels in the lungs and alveolar air, wherein the obtaining step is implemented while the audio frequency driving signal is being applied to the patient's lung;
    identifying a first portion of the power and velocity data that represents movement of interfaces between blood vessels in the lungs and alveolar air that corresponds to a fundamental harmonic, wherein the fundamental harmonic is related to the audio frequency driving signal;
    comparing the identified first portion to a first reference;
    identifying at least one second portion of the power and velocity data that represents movement of interfaces between blood vessels in the lungs and alveolar air that corresponds to at least one higher order harmonic while the audio frequency driving signal is being applied to the patient's lung; and
    comparing the identified at least one second portion to a second reference.

2. The method of claim 1 wherein the audio frequency driving signal is set up by having the patient voice a sound.

3. The method of claim 1 wherein the audio frequency driving signal is set up by activating a transducer that is in acoustic contact with the patient's body.

4. The method of claim 1, wherein, in the obtaining step, the Doppler ultrasound power and velocity data that represents movement of interfaces between blood vessels in the lungs and alveolar air is obtained for a period of time that corresponds to at least one cardiac cycle.

5. The method of claim 1, wherein the audio frequency driving signal includes frequency components between 50 and 1000 Hz.

6. The method of claim 1, further comprising the step of outputting an indication when (a) the fundamental harmonic has a frequency that exceeds a first threshold associated with a diagnosis of acute bronchitis and (b) total power in the at least one higher order harmonic is lower than a second threshold associated with a diagnosis of acute bronchitis.

7. The method of claim 1, further comprising the step of outputting an indication when (a) the fundamental harmonic has a power that is lower than a first threshold associated with a diagnosis of COPD and (b) the total power in the at least one higher order harmonic is higher than a second threshold associated with a diagnosis of COPD.

8. The method of claim 1, further comprising the steps of:
displaying a visual representation of the first portion of the power and velocity data that represents movement of interfaces between blood vessels in the lungs and alveolar air that corresponds to the fundamental harmonic; and
displaying a visual representation of the at least one second portion of the power and velocity data that represents movement of interfaces between blood vessels in the lungs and alveolar air that corresponds to the at least one higher order harmonic.

9. The method of claim 8, further comprising the step of:
correlating a condition in which
(a) the fundamental harmonic has a frequency that is much higher than expected for a normal patient and
(b) total power in the at least one higher order harmonic is much lower than expected for a normal patient with a lung disease.

10. The method of claim 8, further comprising the step of:
correlating a condition in which
(a) the fundamental harmonic has a power that is lower than expected for a normal patient and
(b) total power in the at least one higher order harmonic is higher than expected for a normal patient with a lung disease.

11. The method of claim 1, wherein, in the obtaining step, the Doppler ultrasound power and velocity data that represents movement of interfaces between blood vessels in the lungs and alveolar air is obtained using a beam with an effective cross section of at least ¼ cm².

12. The method of claim 1, wherein, in the obtaining step, the Doppler ultrasound power and velocity data that represents movement of interfaces between blood vessels in the lungs and alveolar air is obtained using a beam with an effective cross section of between ¼ cm² and 3 cm².

13. A method of evaluating the functionality of a patient's lung, the method comprising the steps of:
obtaining, using an ultrasound probe that is aimed at the patient's lung, Doppler ultrasound power and velocity data that represents movement of interfaces between blood vessels in the lungs and alveolar air at a first time after the patient inhales a known quantity of a gas, while an audio signal that includes frequency components between 50 and 1000 Hz is used to induce a vibration in the lung at a resonant frequency of the lung;
determining a first resonant frequency of the lung at the first time based on the power and velocity data that represents movement of interfaces between blood vessels in the lungs and alveolar air obtained at the first time;
obtaining, using an ultrasound probe that is aimed at the patient's lung, Doppler ultrasound power and velocity data that represents movement of interfaces between blood vessels in the lungs and alveolar air at a second time after the patient inhales the known quantity of a gas, while an audio signal that includes frequency components between 50 and 1000 Hz is used to induce a vibration in the lung at a resonant frequency of the lung;
determining a second resonant frequency of the lung at the second time based on the power and velocity data that represents movement of interfaces between blood vessels in the lungs and alveolar air obtained at the second time; and
calculating a diffusion rate of the patient's lung based on the first resonant frequency and the second resonant frequency.

14. The method of claim 13 wherein, in the obtaining steps, the vibration is induced in the lung by the patient's voicing of a sound.

15. The method of claim 13 wherein, in the obtaining steps, the vibration is induced in the lung by activating a transducer that is in acoustic contact with the patient's body.

16. The method of claim 13, wherein, in the obtaining steps, the Doppler ultrasound power and velocity data that represents movement of interfaces between blood vessels in the lungs and alveolar air is obtained for a period of time that corresponds to at least one cardiac cycle.

17. The method of claim 13, further comprising the step of calculating a lung capacity of the patient based on the first resonant frequency and the second resonant frequency.

18. The method of claim 17, wherein the gas is helium.

19. The method of claim 13, wherein, in the obtaining steps, the Doppler ultrasound power and velocity data that represents movement of interfaces between blood vessels in the lungs and alveolar air is obtained using a beam with an effective cross section of at least ¼ cm².

20. The method of claim 13, wherein, in the obtaining steps, the Doppler ultrasound power and velocity data that represents movement of interfaces between blood vessels in the lungs and alveolar air is obtained using a beam with an effective cross section of between ¼ cm² and 3 cm².

* * * * *